US006870155B2

(12) United States Patent
Krasnobaev et al.

(10) Patent No.: US 6,870,155 B2
(45) Date of Patent: Mar. 22, 2005

(54) MODIFIED VORTEX FOR AN ION MOBILITY SPECTROMETER

(75) Inventors: Leonid Ya. Krasnobaev, Newton, MA (US); Stephen N. Bunker, Wakefield, MA (US)

(73) Assignee: Implant Sciences Corporation, Wakefield, MA (US)

( * ) Notice: Subject to any disclaimer, the term of this patent is extended or adjusted under 35 U.S.C. 154(b) by 0 days.

(21) Appl. No.: 10/818,434

(22) Filed: Apr. 5, 2004

(65) Prior Publication Data

US 2004/0227073 A1 Nov. 18, 2004

Related U.S. Application Data (63) Continuation-in-part of application No. 10/754,088, filed on Jan. 7, 2004, which is a continuation-in-part of application No. 10/349,491, filed on Jan. 22, 2003, now Pat. No. 6,828,795, which is a continuation-in-part of application No. 10/295,039, filed on Nov. 14, 2002, which is a continuation-in-part of application No. 10/295,010, filed on Nov. 14, 2002.

(60) Provisional application No. 60/363,485, filed on Mar. 12, 2002, provisional application No. 60/357,618, filed on Feb. 15, 2002, and provisional application No. 60/357,394, filed on Feb. 15, 2002.

(51) Int. Cl.[7] .......................... B01D 59/44; H01J 49/00; H01J 49/40
(52) U.S. Cl. ................. 250/283; 250/282; 250/287
(58) Field of Search .................. 250/282, 283, 250/287

(56) References Cited

U.S. PATENT DOCUMENTS

| | | | | |
|---|---|---|---|---|
| 4,551,624 A | * | 11/1985 | Spangler et al. ............ 250/287 |
| 5,200,614 A | * | 4/1993 | Jenkins ........................ 250/286 |
| 6,073,499 A | * | 6/2000 | Settles ....................... 73/864.81 |
| 6,236,042 B1 | * | 5/2001 | Kato et al. ................... 250/288 |
| 6,586,732 B2 | * | 7/2003 | Lee et al. .................... 250/288 |
| 2003/0193338 A1 | * | 10/2003 | Krasnobaev et al. ......... 324/464 |

OTHER PUBLICATIONS

U.S. Appl. No. 10/890,820 filed Jul. 14, 2004, Flash Vapor Sampling for a Trace Chemical Detector, Belyakov et al.

U.S. Appl. No. 10/853,563 filed May 25, 2004, Pulsed Vapor Desorber, Belyakov et al.

\* cited by examiner

*Primary Examiner*—John R. Lee
*Assistant Examiner*—Kalimah Fernandez
(74) *Attorney, Agent, or Firm*—Choate, Hall & Stewart (57) ABSTRACT

The presence of trace molecules in air is often determined using a well-known device called an ion mobility spectrometer. Such devices are commonly utilized in the fields of explosives detection, identification of narcotics, and in applications characterized by the presence of very low airborne concentrations of organic molecules of special interest. The sensitivity of such instruments is dependent on the method of gas sampling utilized. The vortex sampling nozzle consists of an intake gas flow and a separate coaxial heated, emitted gas flow that is deflected to move with a circular motion. A heated vortex sampling nozzle can greatly improve the sampling efficiency for low volatility target molecules, particularly when the sampling needs to be performed at a distance from the air intake and the vapor pressure of the target molecules is very low. Additionally, the vortex air may contain one or more additional substances that promote vaporization, combine with the target molecule, or provide a known marker in the ion mobility time-of-flight spectrum.

32 Claims, 10 Drawing Sheets

MODIFIED VORTEX FOR AN ION MOBILITY SPECTROMETER

CROSS-REFERENCE TO RELATED APPLICATIONS

This application is a CIP of Ser. No. 10/295,010 Nov. 14, 2002 which claims benefit of 60/357,294 Feb. 15, 2002 and claims benefit of 60/357,618 Feb. 15, 2002 and claims benefit of 60/363,485 Mar. 12, 2002.

This application Ser. No. 10/818,434 is a CIP of Ser. No. 10/295,039 Nov. 14, 2002 which claims benefit of 60/375,394 Feb. 15, 2002 and claims benefit of 60/375,618 Feb. 15, 2002 and claims benefit of 60/363,485 Mar. 12, 2002.

This application Ser. No. 10/818,434 is a CIP of Ser. No. 10/349,491 Jan. 22, 2003, now U.S. Pat. No. 6,828,795 which claims benefit of 60/357,394 Feb. 15, 2002 and claims benefit of 60/357,618 Feb. 15, 2002 and claims benefit of 60/363,485 Mar. 12, 2002.

This application Ser. No. 10/818,434 is a CIP of Ser. No. 10/754,088 Jan. 7, 2004.

BACKGROUND OF THE INVENTION

1. Field of the Invention

This invention relates to an ion mobility spectrometry instrument that detects chemicals present as vapors in air or other gases, or liberated as vapors from condensed phases, such as particles or solutions, and more particularly relates to the sampling of such vapors for injection into the ion source of the ion mobility spectrometer (IMS) when the source of vapors exhibits a relatively low vapor pressure.

2. Description of Related Art

IMS instruments operate on the basis of the time taken by ionized molecules to move through a gas-filled drift region to a current collector while under the influence of an electric field. The ions are created in a gas-filled region called the ion source, which is connected to the drift region through an orifice or a barrier grid. The ion source may use any of a variety of techniques to ionize atoms and molecules. One or more flowing streams of gas enter the ion source through one or more orifices, and the gas may exit through one or more different orifices. At least one of the flowing gas streams entering the ion source includes gas that has been sampled (the "sample gas") from the surrounding atmosphere or other source of vapor to be analyzed.

In some cases, the process of taking a sample begins with an operator rubbing an absorbent substance, such as chemical filter paper, onto the surface to be tested. Particles of the chemical of interest may then be transferred and concentrated on the absorber. This intermediate absorber is then brought to the vicinity of the sampling orifice of the IMS. However, this method of concentrating using an absorbent substance is deficient in that it tends to be relatively slow to implement and is subject to variations in the skill of the operator. Additionally, while the absorber is relatively low in cost, the process of taking a great many samples becomes expensive in that the absorber generally should only be used once to ensure consistent results.

The instrument's sampling method uses a gas pump, which draws the sample gas into the ion source through a tube. For example, the pump may be disposed to provide a partial vacuum at the exit of the ion source. This partial vacuum may be transmitted through the confines of the ion source and appear at the entrance orifice of the ion source. A further tubulation may be provided as an extension to a more conveniently disposed sampling orifice external to the IMS. The operator may place a sample in the near vicinity of this external sampling orifice, and the ambient vapor may be drawn into the gas flow moving towards the ion source.

Sometimes molecules of interest undesirably adsorb onto surfaces in the sampling flow path. Therefore, it is sometimes useful to minimize unnecessary surfaces between the sampling orifice and the ion source. This is why the gas pump is often disposed in the gas flow stream following the ion source, rather than preceding the ion source.

SUMMARY OF THE INVENTION

According to the present invention, a gas sampling system for an ion mobility spectrometer includes a first gas pump providing a first gas flow at a partial gas vacuum compared to ambient gas pressure, a second gas pump providing a second gas flow at a partial gas pressure compared to the ambient gas pressure, a first orifice for the partial gas vacuum which is external to the ion mobility spectrometer, tubulation means connecting the first orifice to the ion mobility spectrometer, at least one second orifice for the partial gas pressure which is concentric and external to the first orifice, heating for the said partial gas pressure, and gas deflection for inducing a rotational vortex motion of the gas flow from the second orifice. The partial gas vacuum may be within 50 millimeters of mercury (50 Torr) of the ambient gas pressure. The partial gas pressure may be within 50 atmospheres of the ambient gas pressure. The gas deflection may be provided by vanes, a surface of at least one of the second orifices, a rotating impeller, a solid surface disposed with its normal axis substantially perpendicular to the axis of the first orifice, or by the gas flow from one of the other second orifices. The said heating modification of the rotating, vortex air of said second gas flow may be provided by an electrically heated resistance element, a source of infrared or visible light photons, a compressed fluid, the Peltier effect, or a chemical flame. Additionally, waste heat from other components associated with the ion mobility spectrometer may be used for said heating. Preferably, the increase over the ambient temperature produced by said heating is at least 10 degrees Centigrade.

According further to the present invention, the modified vortex air, the said second flow, may contain one or more additional substances that are useful for promoting vaporization, chemically combining with the target molecule, or providing a known marker in the ion mobility time-of-flight spectrum. An example of a substance to promote vaporization is water vapor or steam. An example of a chemical for combining with the target molecule is acetone, alcohol, or ammonia vapor. An example of a substance for providing a known marker is ethylene glycol vapor.

According further to the present invention, a compound gas sampling system for an ion mobility spectrometer includes a plurality of gas sampling systems as described herein, the gas sampling systems arranged so that adjacent vortex flows rotate in opposing directions.

The invention applies to an ion mobility spectrometer that uses an external sampling orifice to draw in vapors to be analyzed. In addition to this existing orifice, at least one second orifice is provided which emits gas towards or around the object to be sampled. Said emitted gas is further deflected such that it is induced to move in a circular flow about the axis of the external sampling orifice. When said second orifice is disposed proximal to and substantially coplanar to said external sampling orifice, a further component of the motion of said emitted gas is a net velocity away from the external sampling orifice. This type of vortex is referred to as a projected vortex. When the said at least one second orifice is disposed substantially beyond the end of the external sampling orifice, this type of vortex is referred to as a surrounding vortex.

The spinning motion of the said emitted gas may be referred to as a vortex, cyclone, or a tornado. The spinning motion results in a radially-outward directed centrifugal force that restrains the emitted gas flow from immediately being drawn radially inward into the partial vacuum of the external sampling orifice. Eventually, friction with the surrounding ambient air will slow the emitted gas sufficiently that it will be drawn into the partial vacuum at some distance from the external sampling orifice. Depending on the flow of the emitted gas, this distance can be varied from near the external sampling orifice (low flow) to far from the external sampling orifice (high flow). The vortex motion in effect creates a virtual tube consisting of a surrounding wall of moving gas that behaves like an extension of the tube that formed the external sampling orifice.

The said heating of the said emitted gas may be employed in cooperation with the motion of the vortex flow to enhance the evaporation rate of low volatility particles on a target surface. While hot air will obviously warm the low volatility particles, the effect is significantly enhanced by the vortex flow, which is substantially tangential to the target surface for efficient transfer of heat. This tangential or parallel flow is in contrast to simply blowing hot air straight at the target surface, which would impinge normal to the surface with a much lower transfer of heat to that portion of the target surface where vapors can be drawn into the gas sampling orifice.

BRIEF DESCRIPTION OF THE DRAWING

The invention is described with reference to the several figures of the drawing, in which, FIG. 1 is a schematic of an IMS detector that may be used in connection with the system disclosed herein.

FIG. 2A is a schematic diagram showing a possible embodiment for a radiative target sample heating unit that uses an electrically heated coil of wire at the focus of a parabolic reflector.

FIG. 2B is a schematic diagram showing a possible embodiment for a radiative target sample heating unit that uses a pulsed visible light lamp near the focus of a parabolic reflector.

FIG. 2C is a schematic diagram showing a possible embodiment for a radiative target sample heating unit that uses a toroidal heated coil of wire within a component of a gas cyclone used in gas sampling.

FIG. 2D is a schematic diagram showing a possible embodiment for a radiative target sample heating unit that uses a pulsed visible light lamp within a component of a gas cyclone used in gas sampling.

FIG. 3 shows a possible embodiment showing the focused light beams from a pair of pulsed visible light parabolic reflection modules aimed at a common location in front of the gas sampling orifice of the IMS.

FIG. 4A is a schematic showing a possible embodiment for transmission of the photon beam using fiber optic light guides.

FIG. 4B is a schematic showing a possible embodiment for filtering of the photon beam using a cold mirror.

FIG. 5 is a schematic showing a possible embodiment for scanning the photon beam or beams using one or more moving hot mirrors.

FIG. 6A is a schematic showing gas flow in a conventional gas sampling system not using a cyclonic flow.

FIG. 6B is a schematic showing a cyclone gas sampling system with a cone-shaped nozzle using deflection vanes.

FIG. 6C is a schematic showing a cyclone gas sampling system with a cone-shaped nozzle using tangential gas flow.

FIG. 7 shows a plurality of cyclones arranged in a rectilinear grid.

FIG. 8 shows an embodiment of a cyclone nozzle that may be scanned on at least one axis.

FIG. 9 is a schematic showing a large volume surrounding vortex gas sampling system.

FIG. 10 is a measurement of the relative sensitivity as a function of position for the vortex gas sampling system of the type shown in FIG. 6C.

DETAILED DESCRIPTION

An IMS is illustrated in FIG. 1. While various embodiments may differ in details, FIG. 1 shows basic features of an IMS that may be used in connection with the system described herein. The IMS includes an ion source 1, a drift tube 2, a current collector 3, a source of operating voltage 4 and a source of purified drift gas 5, possibly with it own gas pump 6. An IMS may already include a gas pump for gas sampling 10 and a tubular connection 11 between the ion source 1 and an external gas sampling inlet 20 that includes an orifice. Gas flow for the drift gas 7 moves through the drift tube 2. Sampling gas flow 12 moves from the external gas sampling inlet 20 through the tubular connection 11 and ion source 1 to the gas sampling pump 10.

FIGS. 2A–2D show a selection of possible embodiments for a radiative heating element, provided proximal to the gas sampling inlet 20, that heats the target surface in conjunction with the gas sampling system of the IMS. In FIG. 2A, the technique for heating combines a continuous electrically heated wire 30, which emits substantially in the infrared, with a parabolic reflector 70. The coil of heated wire is disposed at or near the focal point of the reflector in order to form a beam of photons that is substantially parallel. The coil 30 may also be disposed slightly offset of the focal point of the reflector in order to form a beam cross section that is either slightly converging or diverging, depending on the target area of interest. The electrically heated wire 30 is electrically insulated from the reflector 70 by means of insulators 31. The reflector 70 may optionally be polished and optionally coated with a reflective material 71. The electrically heated wire may also be optionally disposed within a sealed enclosure, such as an evacuated transparent glass bulb.

In FIG. 2B, the light source is provided by a miniature pulsed xenon gas-filled lamp 40. A parabolic reflector 70 is shown with a coating of a reflective material 71. In FIG. 2C, a conical reflector 52 is employed which may also be a component of the gas sampling system of the IMS, such as a cyclone nozzle. The infrared radiation is produced by a toroidally-shaped coil of electrically heated wire 50, which is mounted on insulators 51. In FIG. 2D, the reflector is similar to that for FIG. 2C, but the light is provided by a toroidally-shaped pulsed xenon lamp 80 mounted on wires 81.

FIG. 3 shows a possible embodiment in the form of two pulsed visible light lamp modules 61 mounted proximal to the tubular connection 11 to the IMS and to the gas sampling inlet 20. The lamp modules 61 focus their photon beams 18 onto the target surface 15, heating target particles 16 and causing the enhanced emission of target molecule vapors 17. The target molecule vapors 17 are entrained in the gas flow 12 entering the gas sampling inlet 20. Different numbers of the same or different types of heating modules may be used.

Light sources that produce a spectrum of wavelengths substantially in the visible band may optionally be coated, filtered, or covered with infrared-enhancing materials in order to increase the infrared fraction of the output spectrum. Such materials may act as transmission filters in which the infrared component is selectively passed, or they may alternatively convert a portion of the incident visible light photons to infrared photons, possibly by heating a secondary surface to a high temperature. Similarly, evacuated glass bulbs that have output primarily in visible light may have surface coatings, internal gases, or filters to increase the infrared fraction of the output spectrum. The filter, coating, or covering may optionally be in the form of a mirror that selectively reflects infrared, commonly called a "hot mirror". Alternatively, the filter, coating, or covering may be a "cold mirror" that reflects visible but transmits infrared, particularly as a protective window. Such protective windows are useful for isolating hot or delicate sources of light radiation. In addition to a cold mirror, a transparent window or open mesh grid may also be used as a protective window.

Figure 1:
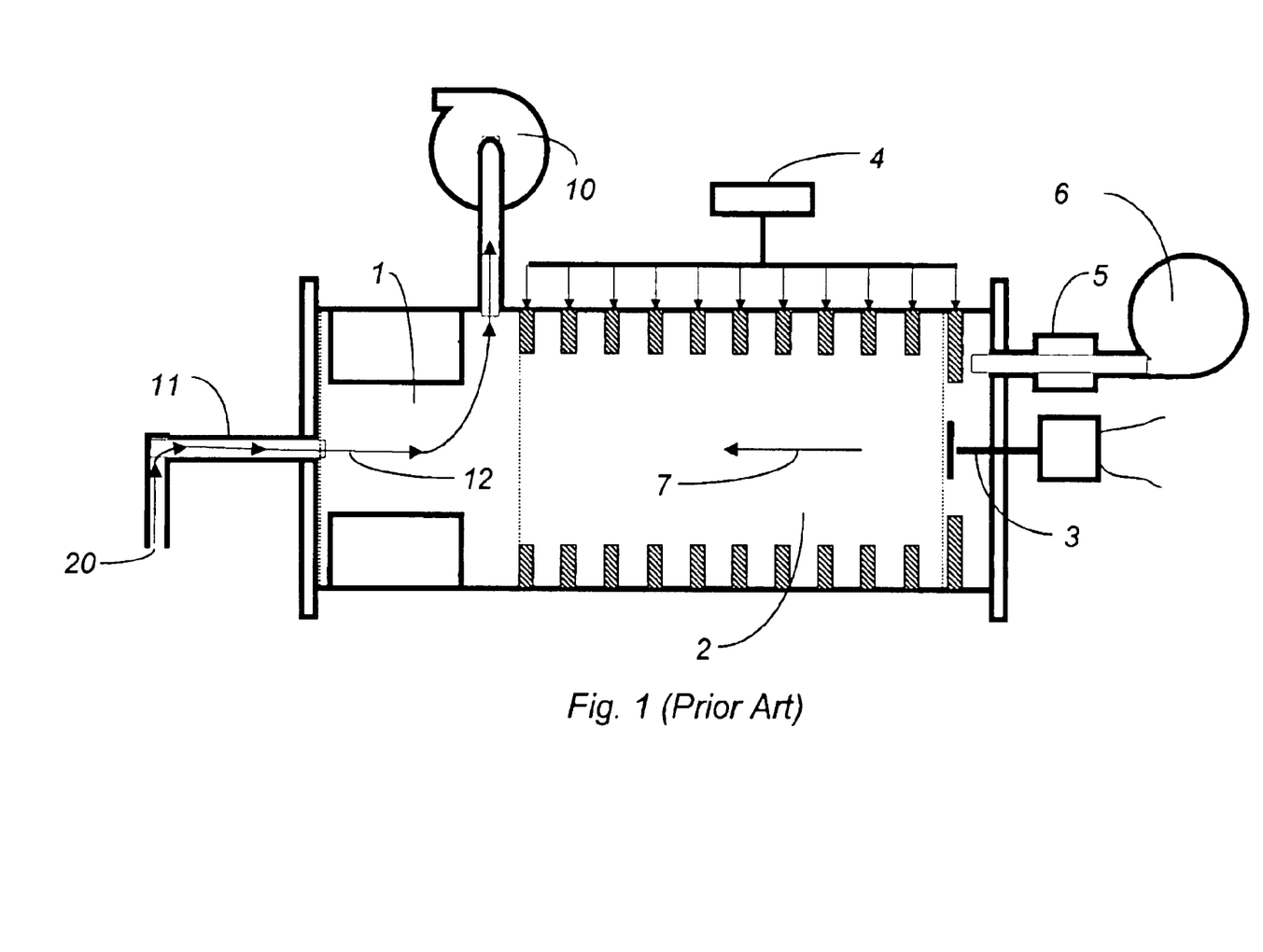
Figure 2A:
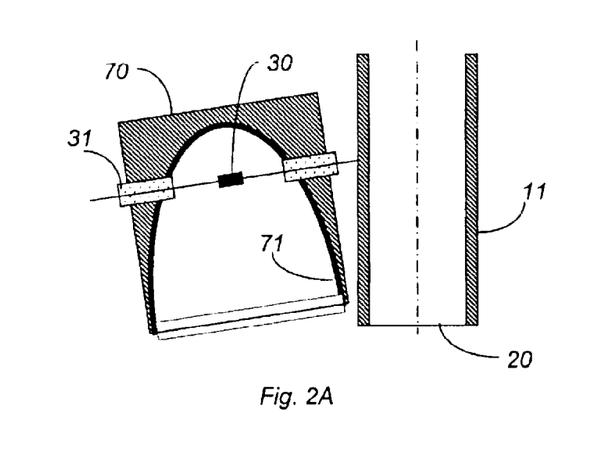
Figure 2B:
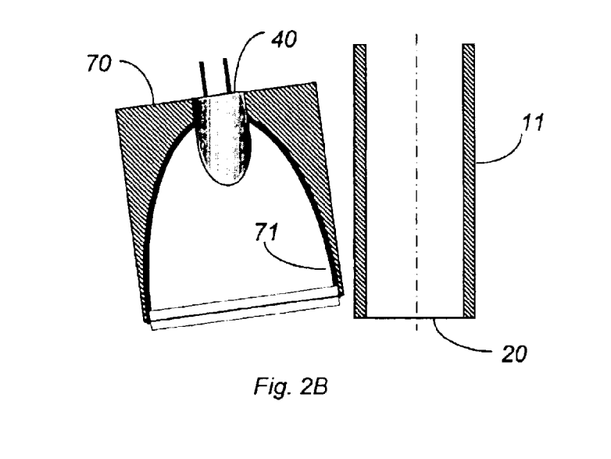
Figure 2C:
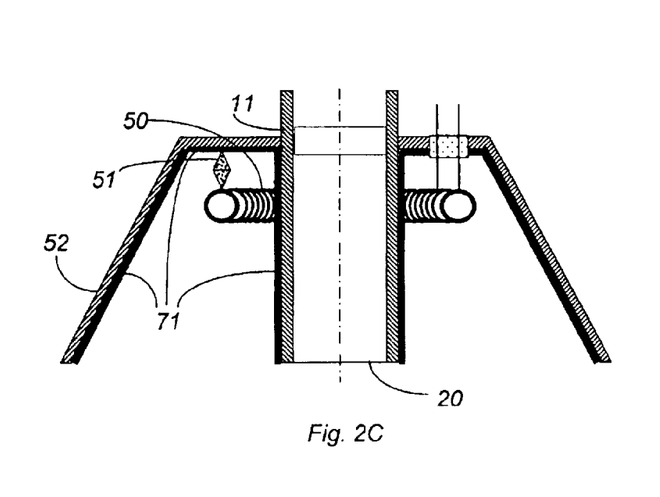
Figure 2D:
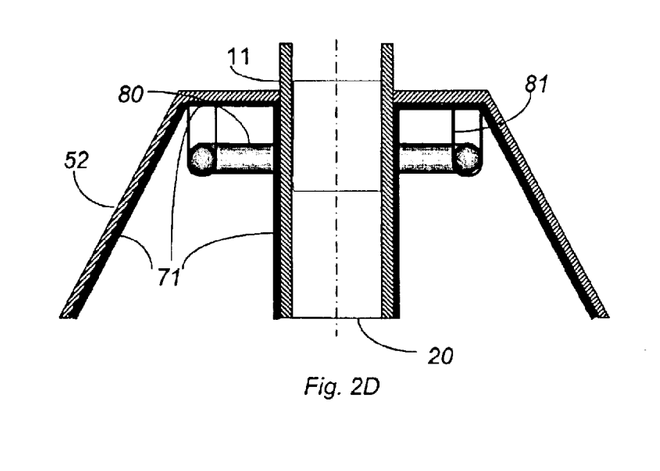
Figure 3:
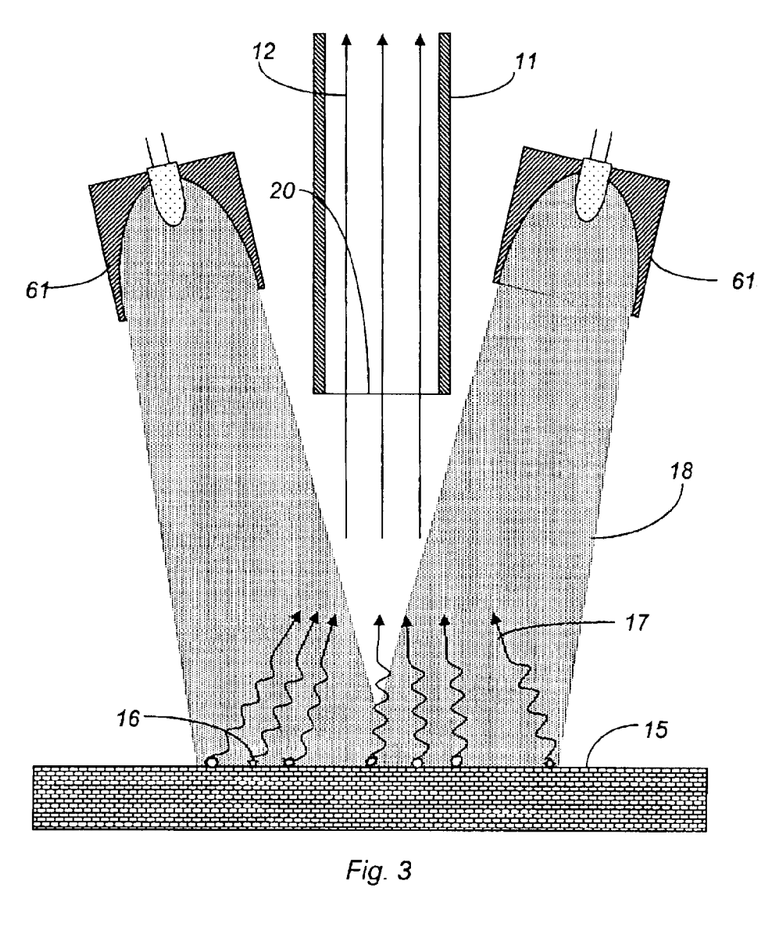
Figure 4A:
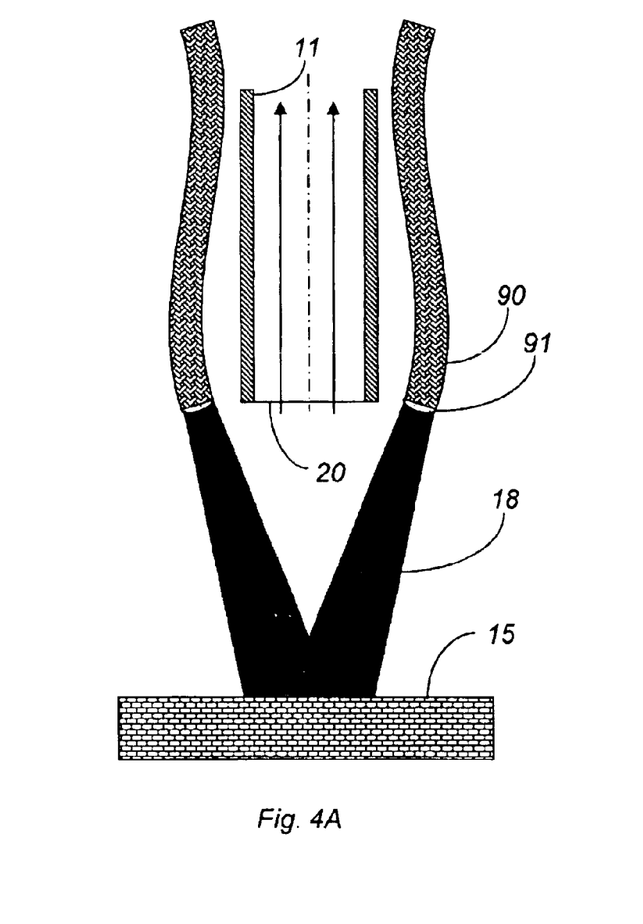
Figure 4B:
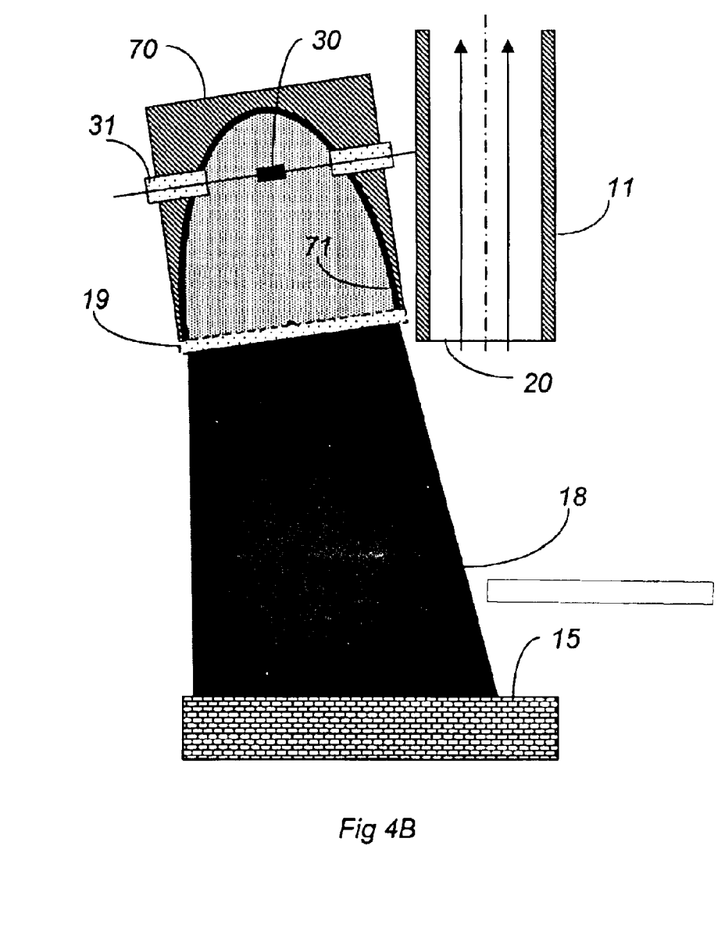

FIGS. 4A and 4B show other possible embodiments for transmitting the photon beam or beams to the target surface 15. In FIG. 4A, fiber optic light guides 90 are disposed proximal to the tubular connection 11 to the IMS and to the gas sampling inlet 20. In the embodiment shown, a lens 91 is employed to minimize the divergence of the photon beam 18 being emitted by the fiber optic cable 90. The photon beams 18 are aimed at positions on the target surface 15 to enhance the emission of target molecule vapor. The positions may optionally be selected to overlap and reinforce one another or to illuminate separate locations. In FIG. 4B, a cold mirror 19 may be employed together with the light module of FIG. 2A in order to enhance the infrared fraction of the photon beam 18.

Fiber optics or similar light guides may be used to separate the location of light generation and the illumination of the target surface to permit physically larger lamps than would be possible nearer to the sampling inlet 20. Moving mirrors may be used to scan the infrared or visible optical beam in order to define a larger irradiated surface area. A variable focus lens or the position of the optical source relative to the mirror may be utilized to change the optical beam cross section or to selectively focus the optical beam at a particular distance.

Figure 5:
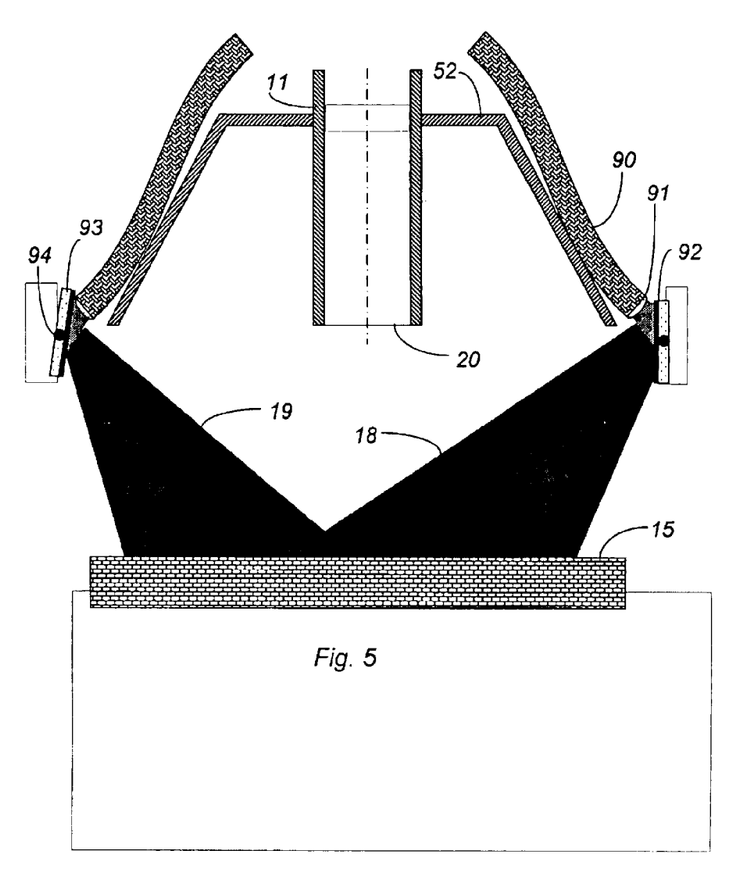

FIG. 5 show a possible embodiment for transmitting the photon beam or beams to the target surface 15 when a conical, hollow nozzle 52 for a cyclone is employed, such as the disclosed in provisional patent application 60/357,394. In this embodiment, hot mirrors 93 reflect the photon beam 18 emitted from fiber optic cables 90. A lens 91 is employed to focus the photon beam 18, although in an alternate embodiment the hot mirror 93 could have a concave surface to accomplish similar focusing control. The hot mirrors 93 may also be optionally tilted about axis 94 in order to scan the photon beam 18 across the target surface 15.

Other methods of optical emission, transmission, filtering, and focusing are possible, and the specifically described embodiments should not be understood as restricting the scope of the invention. In addition, other sampling techniques may be employed and used on their own or in combination with the radiative heating discussed herein.

Figures 6A, 6B:
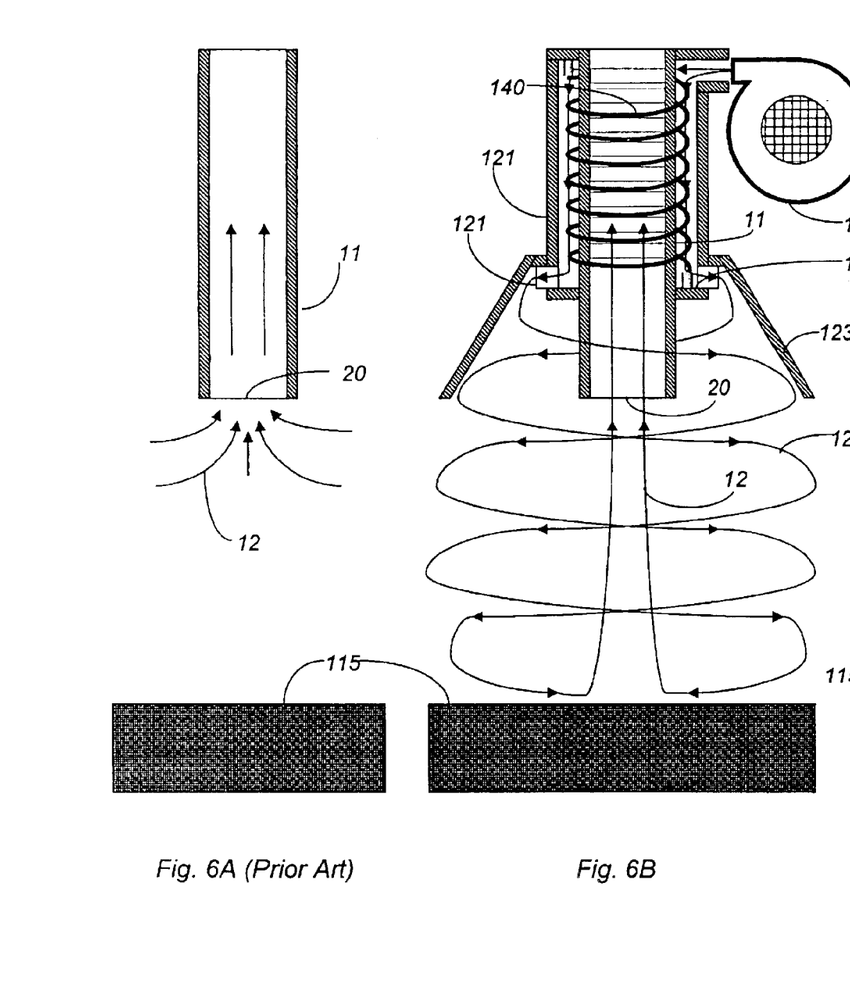

A conventional gas sampling system is shown in FIG. 6A. The gas pump 10 for providing a vacuum may be disposed elsewhere and is not shown in FIG. 6A. The portion of the tubular connection 11 nearest the external gas sampling orifice 20 is shown. The sampling gas flow 12 shows that the volume of gas being sampled is disposed near to the external gas sampling orifice 20, and gas is being drawn into the orifice 20 over an angular range between substantially perpendicular to the axis of the orifice to on the axis of the orifice 20. When a target surface 115 is disposed at a distance greater than one–two times the diameter of the external gas sampling orifice 20, the quantity of sampled gas is either very small or highly diluted by the more abundant gas sampled from nearer the external gas sampling orifice 20.

Figure 6C:
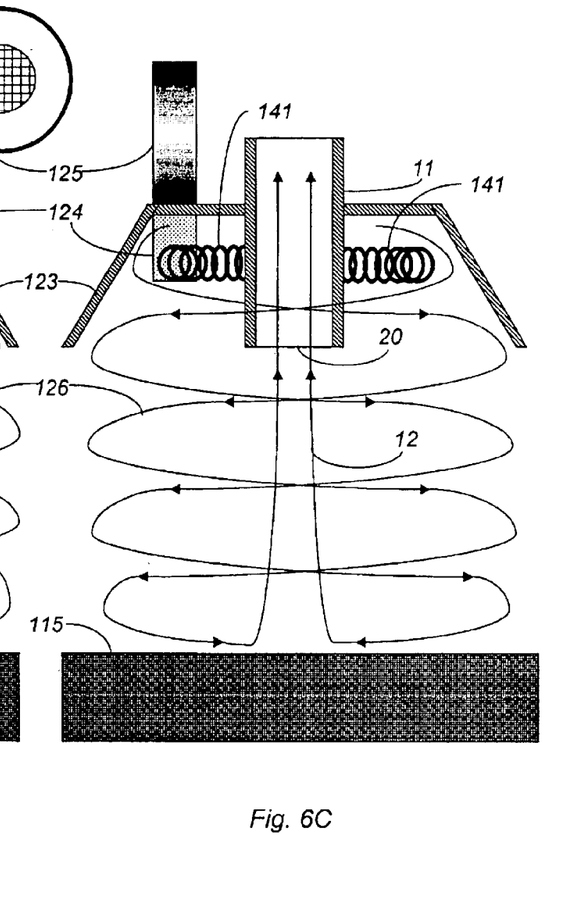

A projected vortex gas sampling system includes a plurality of components as shown in FIGS. 6B and 6C. A partial vacuum relative to ambient gas pressure (supplied by the gas pump 10, not shown in FIG. 6B or 6C) causes the air flow 12. The gas pump 10 may be disposed at some distance from the cyclone gas sampling system with the vacuum being guided to the cyclone gas sampling system by means of the tubulation or conduit 11. The gas pump 10 (not shown) and tubulation 11 may already be part of an existing IMS.

A partial pressure relative to ambient gas pressure may be supplied by a gas pump 125 that provides gas to a second orifice 124 which, in combination with a conical shaped hollow oriface 123 causes a cyclone-like effect of air flow 126. The gas pump 125 may be disposed at some distance from the cyclone gas sampling system with the pressure being guided to the cyclone gas sampling system by means of a tubulation or conduit 121. In an embodiment disclosed herein, the pressure gas pump 125 is separate from the vacuum gas pump 10 to avoid cross-contamination of the sample gas between the two gas flows.

The system may include a heater that heats the airflow from pressure gas pump 125. The heater may be provided by at least one of: an electrically heated resistance element, a source of infrared or visible light photons, a compressed fluid, the Peltier effect, a chemical flame, or by using waste heat from other components of the ion mobility spectrometer. The heater may be disposed inside or on the outside wall of tubulation 121. FIG. 6B shows a heater 140 in series with tubulation 121. FIG. 6C shows a heater 141 within the conical shaped hollow oriface 123. A heater may also be disposed within the structure of the second orifices 124. The system described herein provides for a heated pressure gas flow 126 to move in a circular, cyclonic motion away from the vortex gas sampling system. The system may use gas deflection vanes (not shown) or the hollow, cylindrically or conically shaped orifice 123 that is substantially concentric with the orifice for the partial vacuum 20. The pressure gas flow may be introduced through the second orifice 124, which may be oriented tangential to the hollow cylindrically or conically shaped orifice 123 and may be deflected into a circular flow by means of the curvature of an inside wall thereof. The pressure gas flow orifice 124 may be singular or a plurality of such orifices. The gas pump 125 may also be singular or a plurality of such pumps.

An alternate embodiment is to introduce the pressure gas flow through an orifice 124, which is oriented tangential to the hollow cylindrically or conically shaped orifice 123 and is deflected into a circular flow by means of the curvature of the inside wall. The pressure gas flow orifice 124 may be singular or a plurality of such orifices. The gas pump 125 may also be singular or a plurality of such pumps. Other means for inducing rotary flow of a gas, such as a turbine, mechanically rotating propeller, or impeller, are known in the art and are also included within the scope of the invention.

Figure 7:
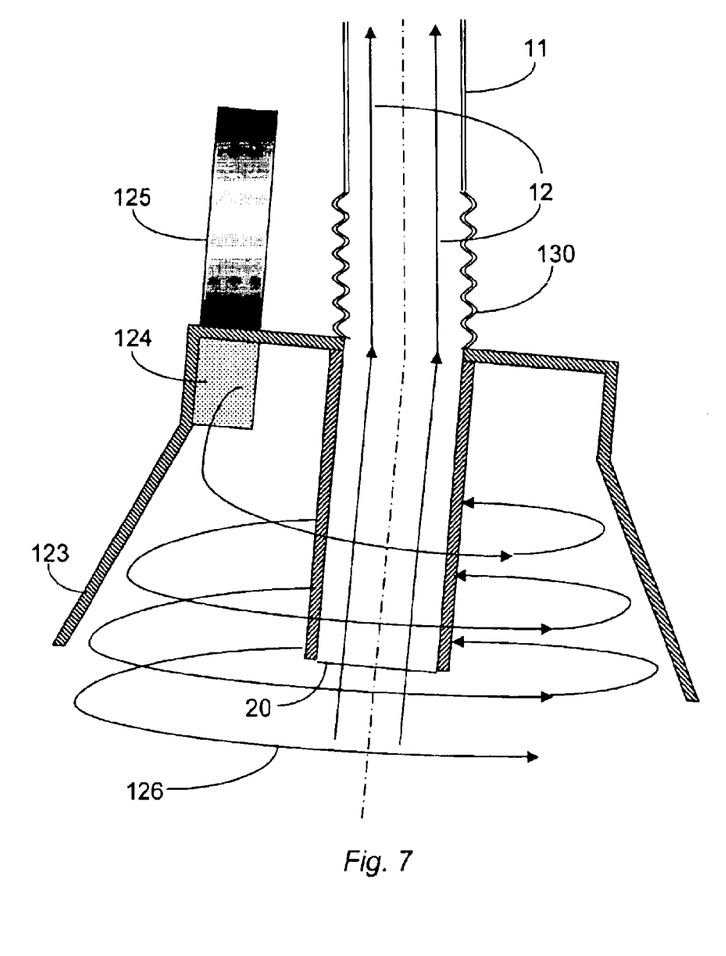

The axis of the emitted cyclonic gas flow may define the axis for guiding the partial vacuum from the external sampling orifice. If the axis of the emitted cyclonic flow is tilted over a small angular range, the partial vacuum due to the flow at the external sampling orifice follows this tilting motion, effectively scanning the position of the virtual gas sampling location. This characteristic is useful for sampling over a one dimensional stripe or a two dimensional surface area without moving the IMS from a fixed location. FIG. 7 shows one possible embodiment of a tilted cyclone in which the gas sampling tubulation 11 is flexible at a location 130. Other possible embodiments would include, but not be limited to a ball joint within tubulation 11, a tilting cylindrical or conical surface 129 with the tubulation 11 fixed, and dynamic control of the relative velocities of a plurality of gas flows 126. As an alternative embodiment, one of the two axes of a two dimensional surface area could be scanned by mechanical movement of the object being scanned, perhaps along a track or moving belt. The second scan axis, perpendicular to the mechanically scanned axis, would be provided by tilting the cyclone orifice. This method is useful for minimizing the number of IMS instruments required to fully sample a given surface.

Cyclonic flow when combined with a vacuum may collect particles. The emitted gas flow generally exhibits a quasi-chaotic motion, which may dislodge larger particles from a surface. Once dislodged, the particles may become entrained in the gas flow towards the external sampling orifice. Depending on the application, such particles may or may not be desirable. For example, particles entering the ion source of the IMS may adhere to surfaces and continue to emit vapor for a long period of time, thus causing a continuous erroneous response. A limited range of particle sizes, about 0.5 to 10 micrometers in diameter, may be removed within the tubulation connecting the external sampling orifice to the ion source using electrostatic precipitation. Larger particles tend to be rejected radially outward due to the centrifugal force of the cyclone gas flow. Smaller particles cannot easily be rejected from the sampled gas.

The problem of contamination from particles may also be lessened by heating the tubulation connecting the external gas sample orifice to the ion source. The ion source may also be heated. Heating causes more rapid vaporization or sublimation of the contamination particles, thus shortening the time period of vapor emission and more rapidly cleansing the gas sampling system. As an alternate embodiment, the tubulation 11 or portions thereof may be designed to be an expendable component that is easily removed for cleaning or replacement.

Another advantage of the cyclone gas sampling method for IMS is that the system is light in weight, which is important for handheld sampling devices. Compared to existing sampling methods, one or more extra gas pumps are needed, but the power requirements are only a few Watts or less for most applications. An extra pump may also serve other functions in the IMS system, such as drawing cooling air from over a heated surface.

Figure 8:
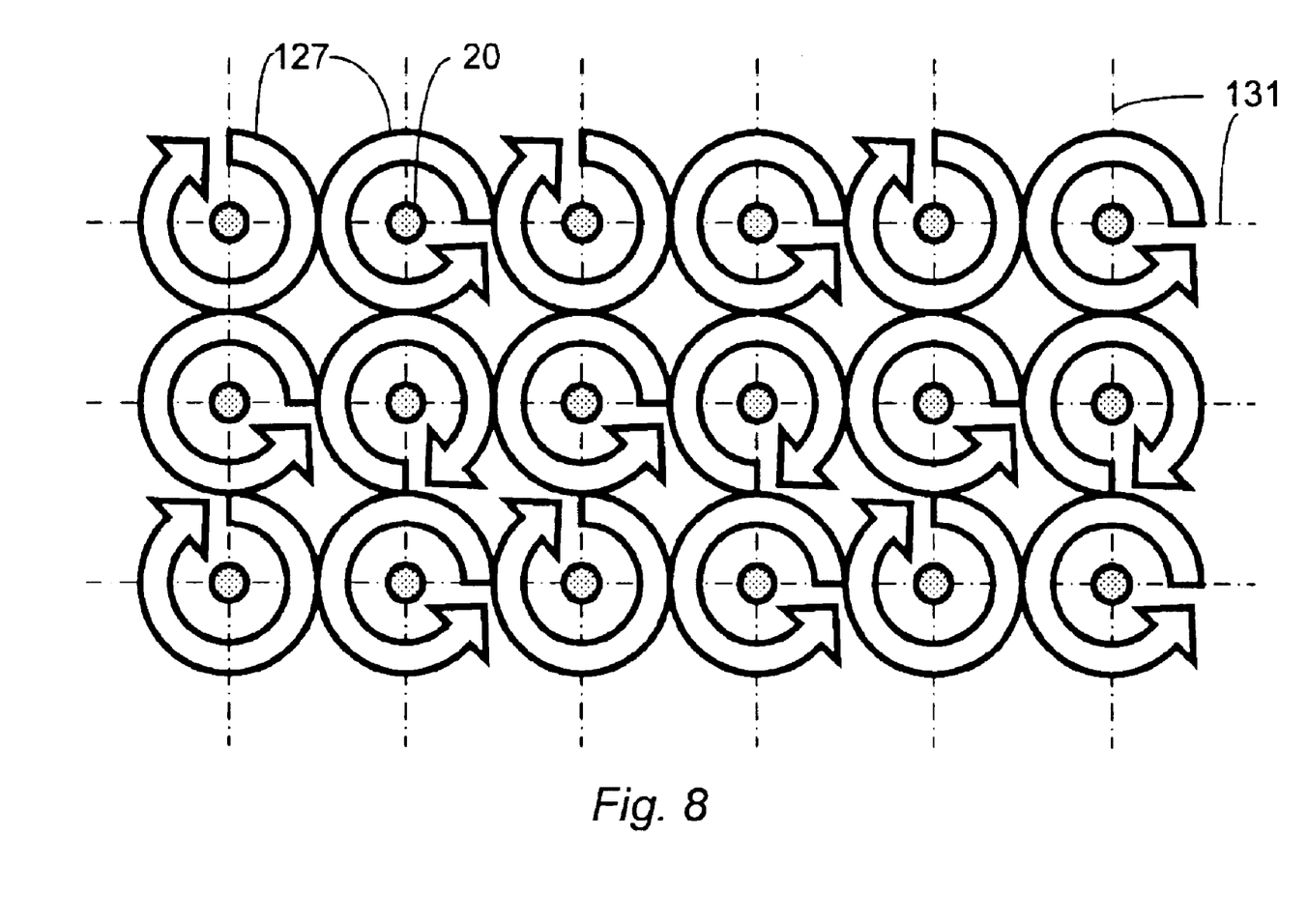

The cyclone sampling system may be utilized singly or by means of a plurality of cyclone sampling systems. The external gas orifice may be a single tubulation connected to a single ion source and IMS or there may be tubular branches leading from a single ion source to greater than one cyclone sampling system. Alternately, multiple ion sources plus IMS's plus cyclone sampling systems may be disposed proximally in order to more efficiently sample a larger surface area in a shorter period of time. FIG. 8 shows one possible layout of a plurality of IMS instruments. In this case a two dimensional grid is used in which the crossing points of the centering lines 131 is the location of an IMS instrument. The external gas sampling orifice 20 is indicated for each instrument. The circular direction of cyclone gas flow 127 is also indicated as preferably alternating clockwise and counterclockwise for neighboring instruments in order for the neighboring gas flows 127 to always be in the same direction.

When cyclone sampling systems are disposed proximally, neighboring cyclones preferably have rotational directions of the cyclonic gas flow that are oppositely oriented in order not to have the gas flows cancel each other at the boundary.

The gas flow of the gas emitted into the cyclone may be deflected into a circular flow by several possible means. Fractions of the total emitted gas flow may be selectively deflected by means of individually oriented vanes, such that the net resulting gas flow is circular. Alternatively, a hollow cone or cylinder may be employed with a gas flow entering the cone or cylinder at a tangential angle. The inside walls of the hollow cone or cylinder then act as the deflector, constraining the gas flow along a circular path while within the confines of the hollow cone or cylinder. When the emitted gas expands beyond the hollow cone or cylinder, the partial vacuum of the external sampling gas orifice provides the force required to constrain the emitted gas flow from moving tangentially away from the central axis.

Figure 9:
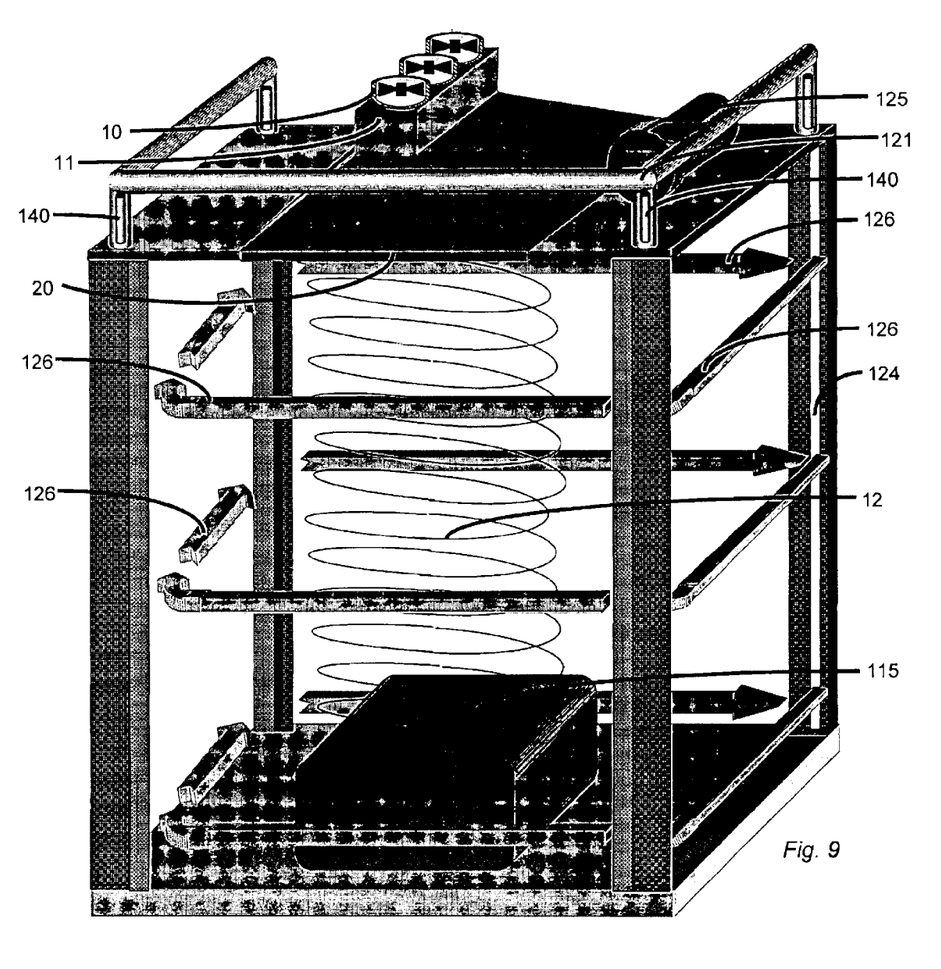

FIG. 9 shows an example of the geometry characteristic of a surrounding vortex. A partial vacuum is provided by the air pump 10 through the tubulation 11, which opens to the ambient air through the first orifice 20. The pressure pump 125 provides airflow through the connecting tubulation 121 to the plurality of the second orifices 124. The heater 140 (such as a cartridge heater) may be disposed inside the tubulation 121. Alternatively, a heater may be disposed on the outside wall of the tubulation 121, as a heating module in series with the tubulation 121, or within the structure of the second orifices 124. The partial pressure heated airflow 126 is deflected into a circular, cyclonic motion when the airflow from each second orifice 124 encounters either the flow from another of the second orifices 124 as shown in FIG. 9 or a solid surface disposed with the normal of the surface disposed perpendicular to the axis of the first orifice 20. The solid surface may be disposed in substantially the same position or slightly further from an axis of the first orifice 20 as the heated airflow 126 from any of the second orifices 124. Said solid surface may either substitute for a portion or all of the heated airflow 126 from the second orifice 124 or it may be used in addition to the heated airflow 126 from the second orifice 124. The heated airflow 126 may be disposed in a mutually clockwise or a mutually counterclockwise orientation relative to the axis of the first orifice 20. The length of the second orifices 124 along the axis of the first orifice 20 may be arbitrarily long, so the volume sampled can be varied over a wide range of sizes.

The target surface 115 may be disposed tangentially to the direction of the airflow 12 of the circular, cyclonic motion. The surface 115 of the rectangular solid shown in FIG. 9 has all of the faces disposed substantially tangential to the airflow 12, except for the underside thereof. Therefore, the heated airflow 126 may significantly improve the efficiency for target vapor emission for the surrounding vortex geometry.

Figure 10:
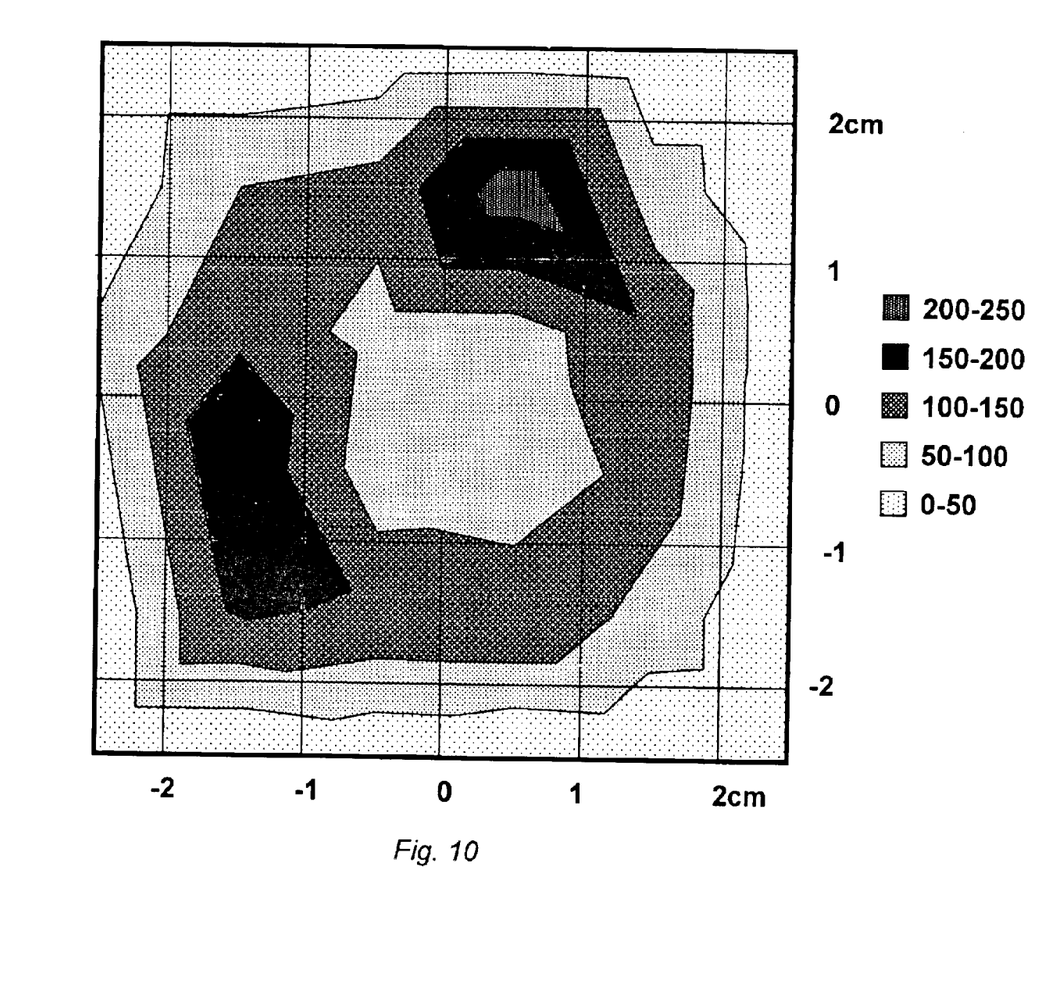

FIG. 10 shows measured data for the projected vortex geometry of FIG. 6C. The data are in the form of a contour plot of the relative sensitivity of an ion mobility spectrometer for detecting a low vapor pressure trinitrotoluene sample. The horizontal and vertical axes represent the position relative to the axis of first orifice 20, which is centered on the central point in the graph. Each square in the grid is one centimeter. It can be seen that the sensitivity is greatest in an annulus around the axis of first orifice 20. This is the location where the heated airflow 126 makes tangential contact with target surface 115.

Another advantage of the heated vortex gas sampling method for IMS is that the system is light in weight, which is important for handheld sampling devices. Compared to existing sampling methods, one or more extra gas pumps are needed, but the power requirements are only a few Watts or less for many applications. An extra pump may also serve other functions in the IMS system, such as drawing cooling air from over a heated surface.

The cyclone sampling system may be utilized singly or by means of a plurality of cyclone sampling systems. The external gas orifice may be a single tubulation connected to a single ion source and IMS or there may be tubular branches leading from a single ion source to greater than one cyclone sampling system. Alternately, multiple ion source plus IMS plus cyclone sampling systems may be disposed proximally in order to more efficiently sample a larger surface area in a shorter period of time. When cyclone sampling systems are disposed proximally, neighboring cyclones preferably have rotational directions of the cyclonic gas flow that are oppositely oriented in order not to have the gas flows cancel each other at the boundary.

The gas flow of the gas emitted into the cyclone may be deflected into a circular flow by several possible means. Fractions of the total emitted gas flow may be selectively deflected by means of individually oriented vanes, such that the net resulting gas flow is circular. Alternatively, a hollow cone or cylinder may be employed with a gas flow entering the cone or cylinder at a tangential angle. The inside walls of the hollow cone or cylinder may then act as the deflector, constraining the gas flow along a circular path while within the confines of the hollow cone or cylinder. When the emitted gas expands beyond the hollow cone or cylinder, the partial vacuum of the external sampling gas orifice provides the force required to constrain the emitted gas flow from moving tangentially away from the central axis. Other methods include a rotational impeller. Methods for creating the required circular airflow may be combined.

Chemical additions may be included within the gas flow from said second orifices. The chemical addition may first have the purpose of inducing a greater vapor pressure from target molecules. An example is the addition of water, either as vapor, steam, or in the form of droplets or mist. The addition of water may increase the vapor concentration over a target molecule, such as trinitrotoluene. A second use of a chemical addition may be to chemically combine with the target molecule. The resultant molecule may exhibit greater vapor pressure, another enhanced property, such as electron affinity, or a more useful value of its ion mobility constant. The purpose of changing the ion mobility constant is either to avoid an interference with another molecule in the time-of-flight ion mobility spectrum or to provide a second independent value for the ion mobility constant, with the two values creating a unique signature for identification. Examples of possible chemical additions of the second type are acetone, alcohol, various types of glycols, and ammonia. A third use of a chemical addition is to add a unique calibration peak into the ion mobility spectrum. An example of this third type of chemical addition is ethylene glycol.

The cyclonic gas flow system described herein may be used in combination with any of the systems disclosed herein for radiative or other heating. For example, the conical reflector 52 used in the embodiment disclosed in FIG. 2C may be also used like the conical shaped orifice 123 of FIGS. 6B and 6C.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A gas sampling system comprising:

a first gas pump that provides a first gas flow at a partial gas vacuum compared to ambient gas pressure;

a second gas pump that provides a second gas flow at a partial gas pressure compared to the ambient gas pressure;

a first orifice that provides said first gas flow;

a plurality of second orifices that provide a plurality of flow members of said second gas flow in a substantially rotational direction that is substantially concentric and both radially and axially external to said first orifice; and a heater that heats at least one flow member of said second gas flow, wherein the gas sampling system provides the first gas flow for analysis within an ion mobility spectrometer.

2. A gas sampling system as in claim 1 wherein said partial gas vacuum is within 50 millimeters of mercury (50 Torr) of the ambient gas pressure.

3. A gas sampling system as in claim 1 wherein said partial gas pressure is within 50 atmospheres of the ambient gas pressure.

4. A gas sampling system as in claim 1, further comprising:

vanes that cause said second gas flow to flow in a substantially rotational direction.

5. A gas sampling system as in claim 1, further comprising:

a hollow member wherein an inside surface thereof causes said second gas flow to flow in a substantially rotational direction.

6. A gas sampling system, according to claim 5, wherein said heater is disposed within said hollow member.

7. A gas sampling system as in claim 1, wherein the said plurality of second orifices directs the said second gas flow in a substantially perpendicular direction with respect to the axis of the said first orifice.

8. A gas sampling system as in claim 7, further comprising:

a solid surface disposed with its normal axis substantially perpendicular to the axis of the said first orifice, wherein said second gas flow flows in a substantially rotational direction due to the deflection of the flow of at least one flow member by said solid surface.

9. A gas sampling system as in claim 7, wherein said second gas flow flows in a substantially rotational direction due to interaction between the flow members.

10. A gas sampling system as in claim 1, further comprising:

a rotating impeller that causes said second gas flow to flow in a substantially rotational direction.

11. A gas sampling system as in claim 1 wherein said rotational direction of all the flow members is mutually clockwise or mutually counter-clockwise relative to the axis of said first orifice.

12. A gas sampling system as in claim 1 wherein the heat for said heater is provided by at least one of electric current resistance or impedance, photon radiation, fluid compression, Peltier effect, and chemical flame or reaction.

13. A gas sampling system as in claim 1 wherein said heater uses waste heat generated by other components of said ion mobility spectrometer.

14. A gas sampling system as in claim 1 wherein said heater increases temperature of said second gas flow from said plurality of second orifices by at least 10 degrees Centigrade from ambient temperature.

15. A gas sampling system, according to claim 1, wherein said heater is a radiative heater.

16. A gas sampling system, according to claim 1, further comprising:

tubulation that couples said second gas pump with said second orifaces.

17. A gas sampling system, according to claim 16, wherein said heater is disposed outside said tubulation.

18. A gas sampling system, according to claim 16, wherein said heater is disposed inside said tubulation.

19. A gas sampling system, according to claim 16, wherein said heater is disposed in series with said tubulation.

20. A gas sampling system, according to claim 1, wherein said heater is disposed within said second orifices.

21. A gas sampling system comprising:

a first gas pump that provides a first gas flow at a partial gas vacuum compared to ambient gas pressure;

a second gas pump that provides a second gas flow at a partial gas pressure compared to the ambient gas pressure;

a first orifice that provides said first gas flow;

a plurality of second orifices that provide a plurality of flow members of said second gas flow in a substantially rotational direction that is substantially concentric and both radially and axially external to said first orifice; and at least one chemical addition into at least one flow member, wherein the gas sampling system provides the first gas flow for analysis within an ion mobility spectrometer.

22. A gas sampling system as in claim 21 wherein said partial gas vacuum is within 50 millimeters of mercury (50 Torr) of the ambient gas pressure.

23. A gas sampling system as in claim 21 wherein said partial gas pressure is within 50 atmospheres of the ambient gas pressure.

24. A gas sampling system as in claim 21, further comprising:

vanes that cause said second gas flow to flow in a substantially rotational direction.

25. A gas sampling system as in claim 21, further comprising:

a hollow member wherein an inside surface thereof cause said second gas flow to flow in a substantially rotational direction.

26. A gas sampling system as in claim 21, wherein the said plurality of second orifices directs the said second gas flow in a substantially perpendicular direction with respect to an axis of the said first orifice.

27. A gas sampling system as in claim 26, further comprising:

a solid surface disposed with its normal axis substantially perpendicular to the axis of the said first orifice, wherein said second gas flow flows in a substantially rotational direction due to the deflection of the flow of at least one flow member by said solid surface.

28. A gas sampling system as in claim 26, wherein said second gas flow flows in a substantially rotational direction due to interaction between the flow members.

29. A gas sampling system as in claim 21, further comprising:

a rotating impeller that causes said second gas flow to flow in a substantially rotational direction.

30. A gas sampling system as in claim 21 wherein said rotational direction of all the flow members is mutually clockwise or mutually counter-clockwise relative to the axis of said first orifice.

31. A gas sampling system as in claim 21 wherein said chemical addition is water in liquid or vapor form.

32. A gas sampling system as in claim 21 wherein said chemical addition is at least one of acetone, alcohol, ethylene glycol, and propylene glycol.

* * * * *